United States Patent [19]

Usami

[11] Patent Number: 4,942,866
[45] Date of Patent: Jul. 24, 1990

[54] BENDING CONTROL APPARATUS FOR ENDOSCOPE

[75] Inventor: Junji Usami, Tokyo, Japan

[73] Assignee: Asahi Kogaku Kogyo Kabushiki K:K., Tokyo, Japan

[21] Appl. No.: 311,730

[22] Filed: Feb. 17, 1989

[30] Foreign Application Priority Data

Feb. 22, 1988 [JP] Japan .............................. 63-22900[U]

[51] Int. Cl.$^5$ ................................................ A61B 1/00
[52] U.S. Cl. .................................................... 128/4
[58] Field of Search .................. 128/4, 6; 74/49, 89.2, 74/89.22

[56] References Cited

U.S. PATENT DOCUMENTS

| | | | |
|---|---|---|---|
| 377,315 | 1/1888 | Mains | 74/49 |
| 3,897,775 | 8/1975 | Furihata | 128/6 |
| 4,617,914 | 10/1986 | Ueda | 128/4 |
| 4,718,407 | 1/1988 | Chikama | 128/4 |

Primary Examiner—William H. Grieb
Attorney, Agent, or Firm—Sandler, Greenblum & Bernstein

[57] ABSTRACT

A control wire which is secured at one end thereof to a bendable portion of the insert part of an endoscope is wound on a pulley which is rotatably provided in a control part, and a manual control device is provided outside the control part so as to be rotatable about a position which is offset from the axis of rotation of the pulley by a distance a. The rotational motion of the manual control device is transmitted to the pulley by a rotational motion transmitting device at a position which satisfies the conditions of $c>a$ and $c>b$, wherein b is the distance from the transmitting device to the axis of rotation of the pulley and c is the distance from the transmitting device to the axis of rotation of the manual control device.

17 Claims, 2 Drawing Sheets

BENDING CONTROL APPARATUS FOR ENDOSCOPE

BACKGROUND OF THE INVENTION

1. Field of the Invention

The present invention relates to an apparatus for controlling bending of a bendable portion of the insert part of an endoscope. More particularly, the present invention pertains to a bending control apparatus for an endoscope which is designed so that a pulley which is wound with a control wire is rotated with a manual control device to pull the control wire to thereby bend the bendable portion.

2. Description of the Related Art

In a typical conventional apparatus of the type described above, a manual control means such as a manual control lever which is used to rotate the pulley is connected directly to the rotary shaft of the pulley. Accordingly, the angle of rotation of the pulley is coincident with that of the manual control means.

However, the maximum effective angle of rotation of a manual control means such as a manual control lever is generally limited to a relatively small angle from the viewpoint of structure or controllability. Accordingly, the diameter of the pulley must be increased in order to increase the angle at which the bendable portion is bent, which results in an increase in the overall size of the control part and hence causes the operability to be impaired a great deal.

SUMMARY OF THE INVENTION

An object of the present invention is to provide a compact bending control apparatus for an endoscope which is designed so that it is possible to increase the angle at which the bendable portion is bent without the need to increase the diameter of the pulley.

Other objects and advantages of the present invention will become apparent from the following detailed description of an illustrated embodiment of the invention.

According to the present invention, there is provided a bending control apparatus for an endoscope comprising: a control wire having one end portion thereof secured to a bendable portion which is bendably provided at the distal end of an insert part of the endoscope; a pulley rotatably provided in a control part, the pulley having the control wire wound thereon; a manual control device provided outside the control part so as to be rotatable about a position which is offset from the axis of rotation of the pulley by a distance a; and a rotational motion transmitting device for transmitting the rotational motion of the manual control device to the pulley at a position which satisfies the conditions of c>a and c>b, wherein b is the distance from the rotational motion transmitting device to the axis of rotation of the pulley and c is the distance from the rotational motion transmitting device to the axis of rotation of the manual control device.

By virtue of the above-described arrangement, wherein the positional relationship between the three elements is set so as to satisfy the conditions of c>a and c>b, the angle of rotation of the pulley which is obtained when the manual control device is rotated becomes greater than the angle of rotation of the manual control device.

BRIEF DESCRIPTION OF THE DRAWINGS

The present invention may be more fully understood from the description of a preferred embodiment of the invention set forth below, together with the accompanying drawings, in which.

DESCRIPTION OF THE EMBODIMENT

One embodiment of the present invention will be described hereinunder in detail with reference to the accompanying drawings.

Figure 1:
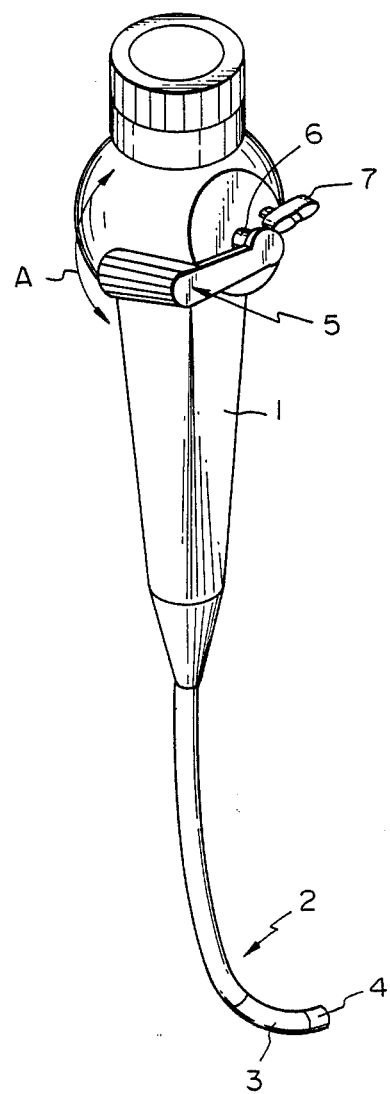
FIG. 1 is a perspective view of an endoscope to which one embodiment of the bending control apparatus according to the present invention is applied.

Referring first to FIG. 1, which is a perspective view showing the general arrangement of an endoscope to which one embodiment of the present invention is applied, the reference numeral 1 denotes a control part, 2 an insert part which is sheathed with a flexible tube, 3 a bendable portion which is formed at the distal end of the insert part 2 such that the bendable portion 3 is bendable by remote control, and 4 a distal end portion which incorporates an objective optical system or the like. The reference numeral 5 denotes a manual control lever which is provided outside the control part 1 such that the lever 5 is pivotal about a shaft 6. As the manual control lever 5 is pivoted, the bending control apparatus according to the present invention which is provided inside the control part 1 is activated to bend the bendable portion 3. The manual control lever 5 is provided so as to be movable within the range shown by the arrow A. The reference numeral 7 denotes a brake lever which is used to suspend the bending control apparatus at a desired position.

Figure 2:
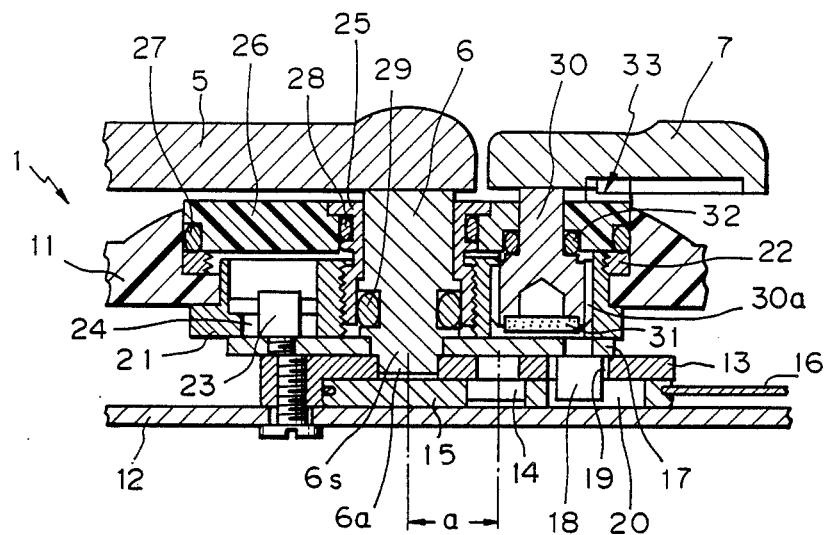
FIG. 2 is a fragmentary sectional view of the endoscope shown in FIG. 1, which illustrates the mechanism of the embodiment of the present invention.

FIG. 2 shows the bending control apparatus according to the present invention. The reference numeral 11 denotes a cover which defines the outer wall of the control part 1. The numeral 12 denotes a frame which is rigidly secured inside the control part 1. A frame member 13 is screwed to the frame 12. A pulley shaft 14 is rigidly press-fitted into the frame member 13. A pulley 15 is provided so as to be rotatable around the pulley shaft 14. The pulley 15 has a bending control wire 16 wound thereon. The wire 16 is fixed to the pulley 15 at one portion thereof, as shown by the reference numeral 16a in FIG. 3 which is a plan view of the pulley 15. Two longitudinal ends of the control wire 16 are secured to the distal end of the bendable portion 3. Accordingly, as the pulley 15 rotates so as to pull the control wire 16, the bendable portion 3 is bent.

The inner end portion 6a of the shaft 6 of the manual control lever 5 is rotatably supported by the frame member 13. The center of the shaft 6 is offset from the center of the pulley shaft 14 by a distance a. A disk 17 is fitted on a square shaft portion 6s of the shaft 6. The disk 17 rotates together with the shaft 6 in one unit.

Figure 3:
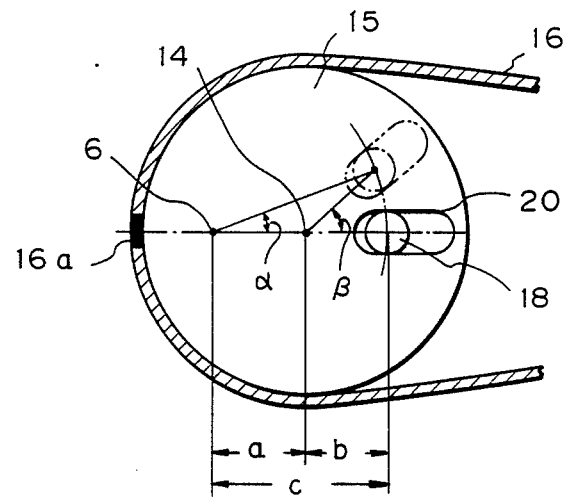
FIG. 3 is a plan view of the pulley employed in the embodiment of the present invention.

The disk 17 is provided with an engagement pin 18. The pin 18 extends through a circular relief groove 19 provided in the frame member 13 and is engaged with a slot 20 which is provided in the pulley 15. The slot 20 is formed such that the longitudinal axis thereof extends in the radial direction of the pulley 15, as shown in FIG. 3. Thus, as the engagement pin 18 revolves around the shaft 6 of the manual control lever 5, the pulley 15 is rotated about the pulley shaft 14. In this embodiment, the engagement pin 18 and the shaft 6 are disposed such that, when the bendable portion 3 is in its neutral position where it is not bent but extends in a straight line, the engagement pin 18 and the shaft 6, together with the pulley shaft 14 interposed therebetween, are placed in a straight line.

The reference numeral 21 denotes a fixed block which is rigidly fastened to the cover 11 by means of a nut 22. A stopper pin 23 which is provided on the disk 17 is movably disposed within a circular groove 24 which is provided in the fixed block 21. Therefore, the angle of rotation of the disk 17 is limited by the stopper pin 23, the travel of which is defined by two longitudinal ends of the groove 24. Thus, the range of pivotal motion of the manual control lever 5, that is, the control stroke of the lever 5, is determined by the stroke of the stopper pin 23. Accordingly, the maximum angle of the bendable portion 3 when bent does not exceed a predetermined angle.

The reference numeral 25 denotes a bearing which rotatably supports the shaft 6 of the manual control lever 5. The bearing 25 is rigidly threaded into the fixed block 21 while pressing a cover member 26 from the outer side. The reference numerals 27, 28 and 29 denote O-rings for sealing.

To the brake lever 7 is connected an actuating shaft 30 having a thread portion 30a which is in threaded engagement with the fixed block 21. The actuating shaft 30 advances in response to the rotation of the brake lever 7, causing a friction plate 31 rigidly secured to the lower end of the shaft 30 to be pressed against the disk 17, thereby braking the rotation of the disk 17. Accordingly, the bendable portion 3 can be maintained in a bent state and it is also possible to control bending of the bendable portion 3 in this state. The reference numeral 32 denotes an O-ring, and 33 a stopper for limiting the range of rotation of the brake lever 7.

The following is a description of the operation of the bending control apparatus for an endoscope according to this embodiment.

As the manual control lever 5 is pivoted, the disk 17 rotates, and the rotation of the disk 17 causes the pulley 15 to rotate through the engagement pin 18, as shown in FIG. 3. As the engagement pin 18 revolves, it moves outward within the slot 20 while causing the pulley 15 to rotate. Accordingly, the pivoting motion of the manual control lever 5 is smoothly transmitted to the pulley 15 which is different from the lever 5 in terms of the position of the axis of rotation.

Since the angle $\beta$ of rotation of the pulley 15 is greater than the angle of rotation of the manual control lever 5, that is, the angle $\alpha$ of revolution of the engagement pin 18, the pulley 15 is rotated through a greater angle than the angle $\alpha$ of rotation of the manual control lever 5. Since in this embodiment the engagement pin 18 and the shaft 6 are disposed such that, when the bendable portion 3 is in its neutral position, the engagement pin 18 and the shaft 6, together with the pulley shaft 14 interposed therebetween, are placed in a straight line, it is possible to rotate the pulley 15 through a greater angle than the angle of rotation of the manual control lever 5 in the vicinity of the neutral position where the control load is lightest.

The above-described operation is obtained when the following conditions are met:

$c > a$ and $c > b$ wherein a is the distance between the axis of rotation of the pulley 15 and that of the manual control lever 5; b is the distance between the axis of rotation of the pulley 15 and the center of the engagement pin 18; and c is the distance between the axis of rotation of the manual control lever 5 and the center of the engagement pin 18.

Accordingly, any bending control apparatus that is arranged such that the conditions of $c > a$ and $c > b$ are satisfied falls under the category of the present invention.

According to the present invention, since the pulley is rotated through a greater angle than the angle of rotation of the manual control device when actuated, it is possible to pull the control wire through a length which is sufficient to obtain a relatively large angle of bending without the need to increase the diameter of the pulley even if the angle of rotation of the manual control device is restricted within a predetermined range. Thus, it is possible to realize a bending control apparatus which has a compact structure and yet provides excellent controllability.

While the invention has been described by reference to a specific embodiment chosen for purposes of illustration, it should be apparent that numerous modifications could be made thereto by those skilled in the art without departing from the basic concept and scope of the invention.

What is claimed is:

1. A bending control apparatus for an endoscope comprising:
   a control wire having one end portion thereof secured to a bendable portion which is bendably provided at the distal end of an insert part of the endoscope;
   a pulley rotatably provided in a control part, said pulley having said control wire wound thereon;
   manual control means provided outside said control part so as to be rotatable about a position which is offset from the axis of rotation of said pulley by a distance a; and
   rotational motion transmitting means for transmitting the rotational motion of said manual control means to said pulley at a position which satisfies the conditions of $c > a$ and $c > b$, wherein b is the distance from said transmitting means to the axis of rotation of said pulley and c is the distance from said transmitting means to the axis of rotation of said manual control means.

2. A bending control apparatus according to claim 1, wherein said rotational motion transmitting means has a pin which revolves around the axis of rotation of said manual control means together with it in one unit and a slot which is provided in said pulley so as to be engaged with said pin.

3. A bending control apparatus according to claim 2, wherein said slot is formed such that the longitudinal axis thereof extends in the radial direction of said pulley.

4. A bending control apparatus according to claim 2, wherein the axis of rotation of said manual control means and said pin are disposed such that, when said bendable portion is in its neutral position where it is not bent but extends in a straight line, the axis of rotation of said manual control means and said pin, together with the axis of rotation of said pulley interposed therebetween, are placed in a straight line.

5. A bending control apparatus according to claim 1, wherein said manual control means is a lever.

6. A bending control apparatus according to claim 1, wherein there is provided means for limiting the control stroke of said manual control means.

7. A bending control apparatus according to claim 1, wherein there is provided means for braking the rotational motion of said pulley to thereby suspend said pulley at a desired rotational position.

8. A driving control apparatus for a wire comprising:
    (a) a control wire;
    (b) a frame;
    (c) means for driving said control wire being rotatably supported on said frame for movement about a first axis of rotation;
    (d) manual control means being rotatably supported on said frame for movement about a second axis of rotation, said second axis of rotation being offset from said first axis of rotation; and
    (e) rotational motion transmitting means cooperating with said manual control means and said means for driving for transmitting the rotational movement of said manual control means to said means for driving.

9. The driving control apparatus according to claim 8, wherein said rotational motion transmitting means causes said means for driving to rotate through a greater angle of rotation than the corresponding angle of rotation of said manual control means.

10. The driving control apparatus according to claim 8, wherein said rotational rotation transmitting means transmits the rotational movement of said manual control means to the driving means at a position which satisfies the conditions of $c > a$ and $c > b$, wherein a is the distance between said first axis of rotation and said second axis of rotation, b is the distance from said rotational transmitting means to said first axis of rotation, and c is the distance between from said rotational transmitting means to said second axis of rotation.

11. The driving control apparatus according to claim 8, wherein said means for driving includes a pulley.

12. The driving control apparatus according to claim 11, wherein said rotational motion transmitting means includes a pin which revolves around said second axis of rotation of said manual control means together with it in one unit and a slot which is provided in said pulley so as to be engaged with said pin.

13. The driving control apparatus according to claim 12, wherein said slot is formed such that the longitudinal axis thereof extends in a radial direction of said pulley.

14. The driving control apparatus according to claim 12, wherein said second axis of rotation and said pin are disposed such that, when said control apparatus is in a neutral position, said second axis of rotation and said pin, together with said first axis of rotation are in a straight line.

15. The driving control apparatus according to claim 8, wherein said manual control means is a lever.

16. The driving control apparatus according to claim 8, further including means for limiting the control stroke of said manual control means.

17. The driving apparatus according to claim 8, further includes means for braking the rotational motion of said means for driving to thereby hold said means for driving at a desired rotational position.

* * * * *

UNITED STATES PATENT AND TRADEMARK OFFICE
CERTIFICATE OF CORRECTION

PATENT NO. : 4,942,866

DATED : July 24, 1990

INVENTOR(S) : Junji USAMI

It is certified that error appears in the above-identified patent and that said Letters Patent is hereby corrected as shown below:

Column 3, line 29, change "thread" to ---threaded-- before "portion".

Column 5, line 29, in claim 10, line 2, change "rotation" to ---motion---.

Column 6, line 3, in claim 10, line 9, delete "between".

Signed and Sealed this

Thirtieth Day of June, 1992

Attest:

DOUGLAS B. COMER

*Attesting Officer*    *Acting Commissioner of Patents and Trademarks*